(12) United States Patent
Jindo

(10) Patent No.: US 7,628,956 B2
(45) Date of Patent: Dec. 8, 2009

(54) SHEATH FLOW FORMING DEVICE AND SAMPLE ANALYZER PROVIDED WITH SAME

(75) Inventor: Katsuhiko Jindo, Kakogawa (JP)

(73) Assignee: Sysmex Corporation, Kobe-shi (JP)

(*) Notice: Subject to any disclaimer, the term of this patent is extended or adjusted under 35 U.S.C. 154(b) by 666 days.

(21) Appl. No.: 10/946,061

(22) Filed: Sep. 22, 2004

(65) Prior Publication Data
US 2005/0074364 A1  Apr. 7, 2005

(30) Foreign Application Priority Data
Oct. 3, 2003 (JP) ............................. 2003-346023

(51) Int. Cl.
*G01N 21/00* (2006.01)
(52) U.S. Cl. .................... 422/81; 422/68.1; 422/73; 422/82.05; 73/1.35; 73/1.36; 73/864.21; 73/864.87; 417/560; 324/71.4
(58) Field of Classification Search ............... 422/68.1, 422/73, 81, 82.05; 73/1.35, 1.36, 864.21, 73/864.87; 417/560; 324/71.4
See application file for complete search history.

(56) References Cited

U.S. PATENT DOCUMENTS

| | | | |
|---|---|---|---|
| 4,695,431 A * | 9/1987 | Farrell | 422/81 |
| 4,977,517 A * | 12/1990 | Gibbs et al. | 702/51 |
| 5,728,351 A | 3/1998 | Carver | |
| 5,882,599 A * | 3/1999 | Gilbert | 422/100 |
| 6,804,984 B2 * | 10/2004 | Shibata | 73/1.36 |
| 2003/0129090 A1 | 7/2003 | Farrell | |

FOREIGN PATENT DOCUMENTS

JP  9-288053 A  11/1997

* cited by examiner

*Primary Examiner*—Lyle A Alexander
*Assistant Examiner*—Dennis M White
(74) *Attorney, Agent, or Firm*—Birch, Stewart, Kolasch & Birch, LLP

(57) ABSTRACT

The sheath flow forming device includes: a container for storing sample fluid and having a supply port for supplying the sample fluid; a second container for storing sheath fluid and having a supply port for supplying the sheath fluid; a flow cell having a sample fluid inlet for receiving sample fluid supplied from the supply port of the first container, a sheath fluid inlet for receiving the sheath fluid from the supply port of the second container, and an outlet for discharging the mixture of the sheath fluid and the sample fluid; a first pump for supplying a sheath fluid to the sheath fluid inlet; a second pump for suctioning fluid within the flow cell through the outlet of the flow cell; and a first drive source for driving the first pump and second pump.

13 Claims, 6 Drawing Sheets

SHEATH FLOW FORMING DEVICE AND SAMPLE ANALYZER PROVIDED WITH SAME

This Nonprovisional application claims priority under 35 U.S.C. § 119(a) on Patent Application No(s). 2003-346023 filed in Japan on Oct. 3, 2003, the entire contents of which are hereby incorporated by reference.

BACKGROUND OF THE INVENTION

1. Field of the Invention

The present invention relates to a sheath flow forming device and sample analyzer provided with same.

2. Background

A particle analyzer (refer to Japanese Laid-Open Patent Publication No. 9-288053) is a known prior art related to the present invention and includes a container for accumulating a sample liquid containing particles to be analyzed and having a nozzle extending downward from the bottom part, a flow cell into which the tip of the nozzle is inserted, a first pump for injecting into the flow cell a first flow quantity Q1 of a sheath fluid which encapsulates a sample fluid flow injected from the nozzle, and an imaging means for imaging particles in the sample fluid encapsulated in the sheath fluid flowing through a transparent container formed on the downstream side of the flow cell, wherein the top part of the sample fluid container is open to the air, and a second pump is provided for suctioning fluid in the flow cell downstream from the transparent tube path of the flow cell, such that the sample fluid flow quantity Qs is determined by (Q2−Q1) when the injection quantity of the first pump is designated Q1 and the suction quantity of the second pump is designated Q2.

In this conventional device, the sample fluid flow quantity Qs is determined by the difference in the flow quantities of the pumps (Q2−Q1). When one flow quantity changes due to a change in the drive sources of the first and second pumps, the flow quantity Qs fluctuates greatly since the flow quantity Qs is quite small (for example, 1/100) compared to the flow quantities Q1 and Q2. Accordingly, problems arise when this occurs inasmuch as the particle flow in the sample fluid becomes unstable, the measurement accuracy is reduced, and at times measurement becomes impossible.

SUMMARY OF THE INVENTION

In view of these problems, the present invention provides a sheath flow forming device and sample analyzer provided with same, which are capable of normally maintaining a constant flow quantity Qs even when the flow quantities Q1 and Q2 change due to the influence of the drive source of the pumps.

The sheath flow forming device embodying features of the present invention includes: (a) a container for storing sample fluid and having a supply port for supplying the sample fluid; (b) a second container for storing sheath fluid and having a supply port for supplying the sheath fluid; (c) a flow cell having a sample fluid inlet for receiving sample fluid supplied from the supply port of the first container, a sheath fluid inlet for receiving the sheath fluid from the supply port of the second container, and an outlet for discharging the mixture of the sheath fluid and the sample fluid; (d) a first pump for supplying a sheath fluid to the sheath fluid inlet; (e) a second pump for suctioning fluid within the flow cell through the outlet of the flow cell; and (f) a first drive source for driving the first pump and second pump.

The sample analyzer embodying features of the present invention includes: (a) a first container for storing sample fluid and having a supply port for supplying the sample fluid; (b) a second container for storing sheath fluid and having a supply port for supplying the sheath fluid; (c) a flow cell having a sample fluid inlet for receiving sample fluid supplied from the supply port of the first container, a sheath fluid inlet for receiving the sheath fluid from the supply port of the second container, and an outlet for discharging the mixture of the sheath fluid and the sample fluid; (d) a first pump for supplying a sheath fluid to the sheath fluid inlet; (e) a second pump for suctioning fluid within the flow cell through the outlet of the flow cell; (f) a first drive source for driving the first pump and second pump; (g) a light source for irradiating with light the sample fluid in the flow cell; (h) detection unit for detecting optical information from the sample fluid; and (i) analysis unit for analyzing the detected optical information.

DETAILED DESCRIPTION OF THE INVENTION

Embodiments of the sample analyzer of the present invention are described hereinafter based on the drawings. In the following embodiments, a particle image analyzer is described as an example of the sample analyzer of the present invention. The present invention is not limited to the given examples.

Flow System and Optical System of the Particle Image Analyzer

Figure 1:
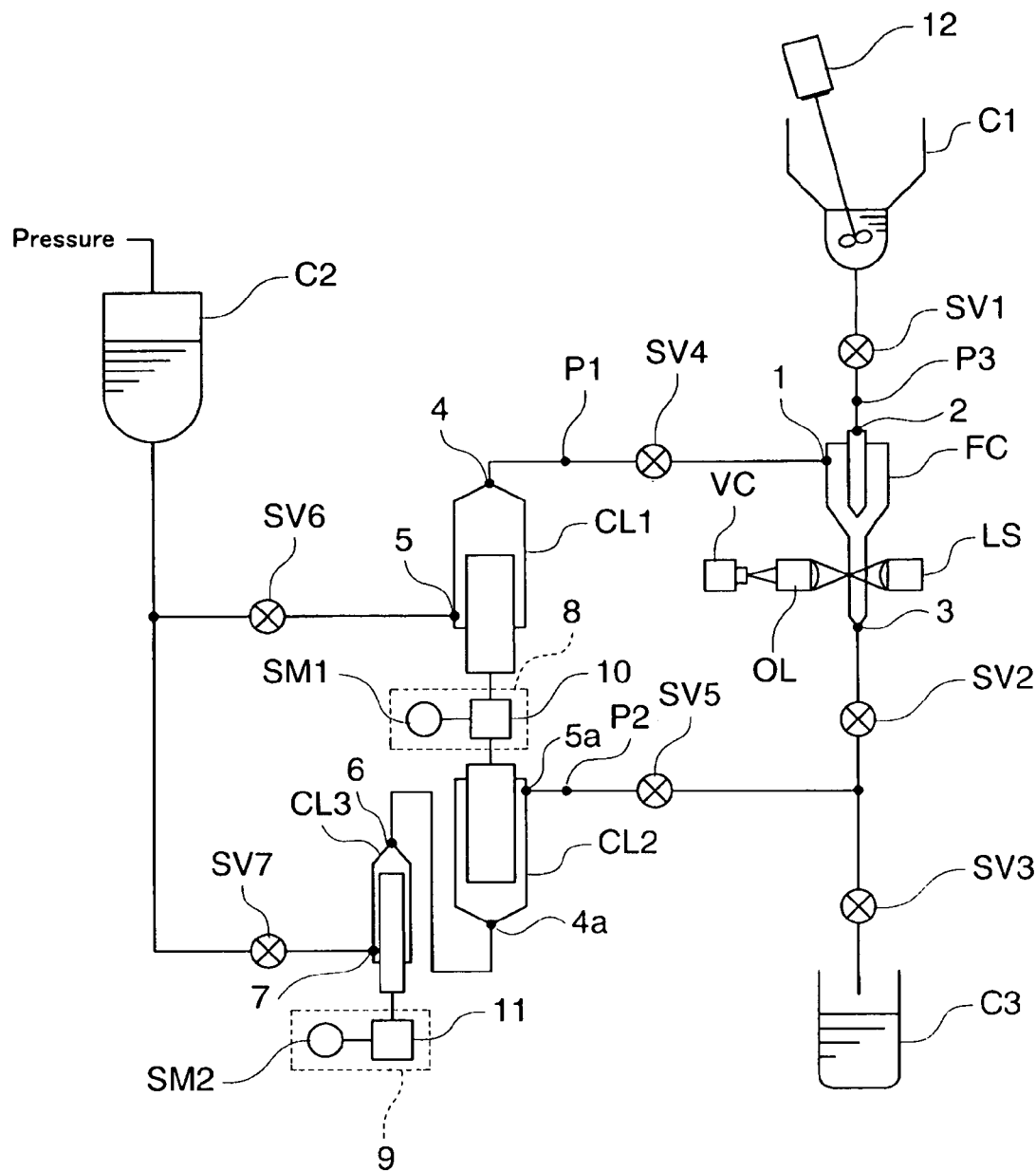
FIG. 1 shows the flow system and optical system of an embodiment of the sample analyzer.

FIG. 1 shows the flow system and optical system of an embodiment of the sample analyzer of the present invention.

As shown in FIG. 1, a sheath flow cell FC is provided with a sheath fluid inlet 1, sample fluid inlet 2, and outlet 3 for discharging the mixture of the sheath fluid and sample fluid. A sample container C1 stores sample fluid through an open top, and an outlet provided in the bottom part is connected to a sample fluid inlet 2 through a flow path. An electromagnetic valve (hereinafter referred to as "valve") SV1 is provided in the flow path between the outlet of the sample container C1 and the sample fluid inlet 2. Furthermore, a mixing device 12 is provided for mixing the sample fluid within the sample fluid container C1.

A syringe pump CL1 has a discharge port 4, and a sheath fluid supply port 5. The discharge port 4 is connected to the sheath fluid inlet 1 of the sheath flow cell EC through a flow path. A valve SV4 is provided in the flow path between the discharge port 4 and the sheath fluid inlet 1. A sheath fluid container C2 stores sheath fluid in its interior, an outlet provided in the bottom part of the container is connected to a sheath supply port 5 through a flow path. A valve SV6 is provided in the flow path between the outlet of the sheath fluid container C2 and the sheath fluid supply port 5.

A syringe pump CL2 is provided with a suction port 5a, and a syringe pump CL3 is provided with two suction ports 6, and a sheath fluid supply port 7. The discharge port 4a of the syringe pump CL2 is connected to the suction port 6 of the syringe pump CL3.

The outlet 3 of the sheath flow cell FC is connected to the suction port 5a of the syringe pump CL2 through a flow path, and is connected to the opening on the open top part of the discharge fluid container C3. Valves SV2 and SV5 are provided in the flow path between the outlet 3 and the suction port 5a. Valves SV2 and SV3 are provided in the flow path between the outlet 3 and the opening of the discharge fluid container C3.

The sheath fluid supply port 7 of the syringe pump CL3 is connected to the outlet of the sheath fluid container C2. A valve SV7 is provided in the flow path between the sheath fluid supply port 7 and the outlet of the sheath fluid container C2.

The syringe pumps CL1 and CL2 are driven in linkage with a single first drive source 8, and the syringe pump CL3 is driven by a second drive source 9. The first drive source 8 is provided with a stepping motor SM1, and a transmission mechanism 10 for converting the rotational movement of the motor SM1 to linear movement and transmitting the linear movement to the syringe pumps CL1 and CL2. The transmission mechanism 10 includes a drive pulley attached to the drive shaft of the stepping motor SM1, and a driven pulley about which is reeved a timing belt, and converts the rotational movement of the stepping motor SM1 to linear movement.

The second drive source 9 is provided with a stepping motor SM2, and a transmission device 11 for converting the rotational movement of the stepping motor 2 to linear movement and transmitting the linear movement to the syringe pump CL3. The transmission mechanism 11 includes a drive pulley attached to the drive shaft of the stepping motor SM2, and a driven pulley about which is reeved a timing belt, and converts the rotational movement of the stepping motor SM2 to linear movement.

Furthermore, A light source LS for irradiating with light the sample fluid flow which is severely constricted as it is surrounded in the sheath fluid, and an objective lens OL and CCD camber VC for imaging the particles in the sample fluid flow are provided in the sheath flow cell FC. The light source LS is a strobe lamp.

Syringe Pump and Drive Source Structures

Figure 2:
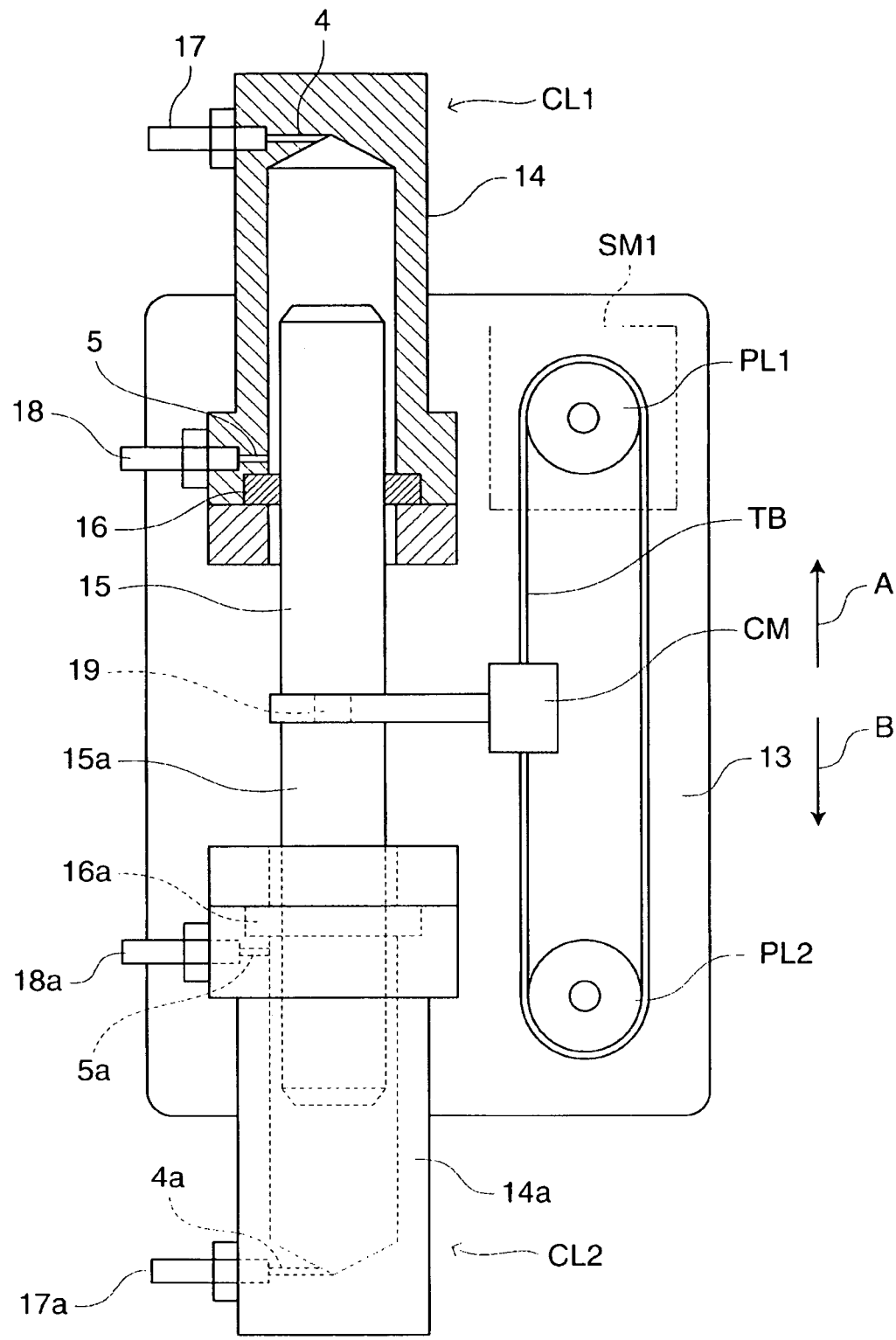
FIG. 2 shows the essential structure of the embodiment of the sample analyzer.

FIG. 2 shows details of the structure of the first drive source 8 shown in FIG. 1. As shown in the drawing, the syringe pumps CL1 and CL2 have the same structure and dimensions, and are fixedly attached to the surface of a support plate 13 in series and in mutually opposing directions. The syringe pump CL1 is provided with a cylinder 14, piston 15 the tip of which is inserted into the cylinder 14, packing 16 for providing an airtight seal of the gap between the cylinder 14 and piston 15, discharge port 4, and nipples 17 and 18 respectively provided at the sheath fluid supply ports 5.

Furthermore, the syringe pump CL2 is provided with a cylinder 14a, piston 15a the tip of which is inserted into the cylinder 14a, packing 16a for providing an airtight seal of the gap between the cylinder 14a and piston 15a, discharge port 4a, and nipples 17a and 18a respectively provided at the suction ports 5a. The pistons 15 and 15a have mutually identical diameters.

The respective back ends of the pistons 15 and 15a are linked by a linkage 19 such that both have the same axis. The stepping motor SM1 is fixedly attached to the back surface of the support plate 13 such that the output shaft of the motor extends from the surface of the support plate 13, and an output shaft drive pulley PL1 is provided.

Furthermore, a corresponding driven pulley PL2 is provided on the front surface of the support plate 13, and a timing belt TB is reeved between the drive pulley PL1 and the driven pulley PL2 so as to be tensioned parallel to the pistons 15 and 15a. The timing belt TB and linkage 19 are connected by a connecting member CM.

When the stepping motor SM1 rotates, the connecting member CM moves linearly in the axial direction (arrow A or arrow B direction) of the pistons 15 and 15a by the timing belt TB. That is, the drive force and driven pulley PL1, PL2, and the timing belt TB from a transmission mechanism for converting the rotational movement of the stepping motor SM1 to linear movement in the arrow A or arrow B direction, and transmit the this linear movement to the syringe pumps CL1 and CL2 at the same time.

When the pistons 15 and 15a move in the arrow A direction, the syringe pump CL1 performs a discharge operation, and the syringe pump CL2 performs a suction operation. When the pistons 15 and 15a move in the arrow B direction, the syringe pumps CL1 and CL2 performs the respectively opposite operations.

Control System

Figure 3:
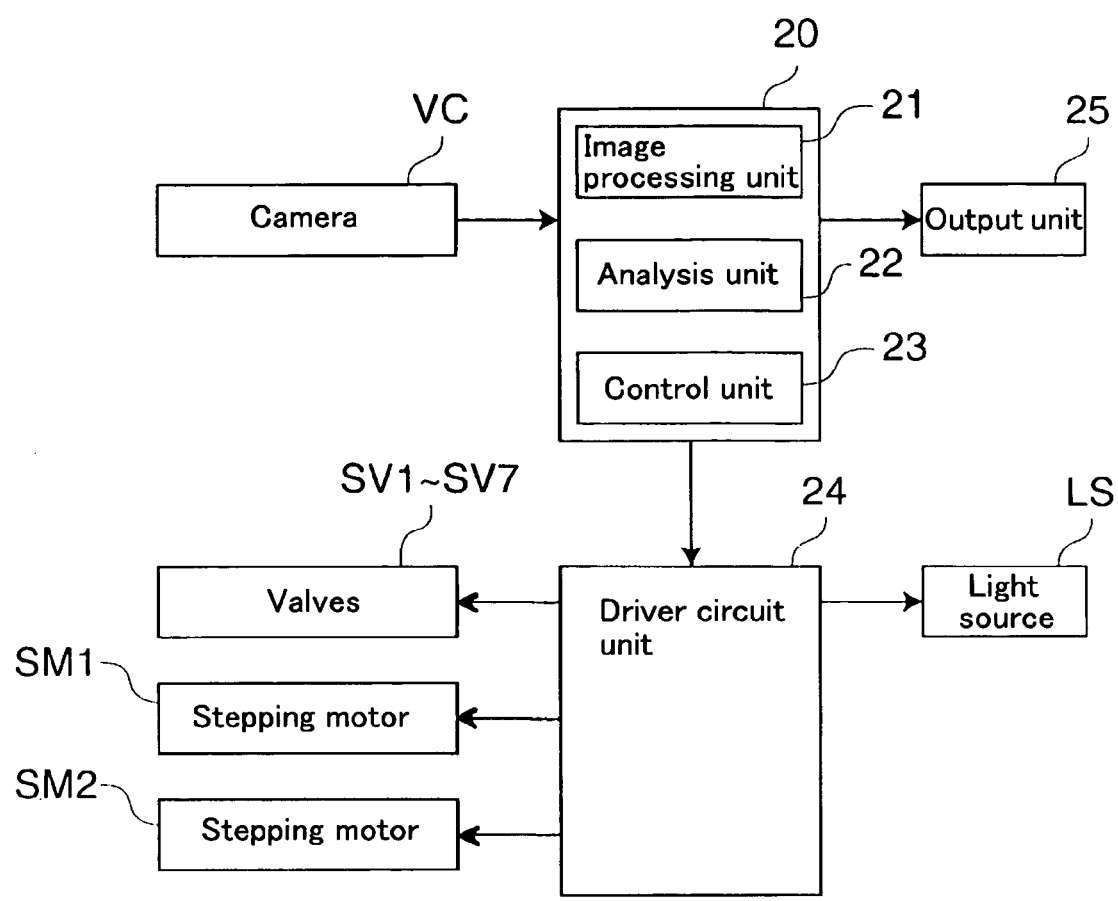
FIG. 3 is a block diagram of the control system of the embodiment of the sample analyzer.

FIG. 3 is a block diagram of the control system of the sample analyzer shown in FIG. 1. A personal computer 20 is provided with an image processing unit 21 for acquiring image signals from a CCD camera VC and performing image processing to generate particle image data, analysis unit 22 for recognizing the particles from the particle shape and coloration, counting the particles and statistically analyzing the particles, and control unit 23 for controlling a driver circuit unit 24. The analysis result of the analysis unit 22 is output from an output unit 25. The driver circuit unit 24, which is controlled by the control unit 23, is provided with driver circuits for the valves SV1 through SV7, stepping motors SM1 and SM2, and light source LS, respectively. The output unit 25 is a CRT. The driver circuit which drives the light source LS is controlled such that the light source LS emits light at predetermined periods.

Analysis Operation

The analysis operation of the sample analyzer having the previously described structure is described below.

In FIG. 1, the syringe pump CL1 is set in the state in which the piston 15 is drawn from the cylinder 14 (discharge operation enabled state), and the syringe pump CL2 is set in the state in which the piston 15a is pushed into the cylinder 14a (suction operation enabled state). Furthermore, the syringe pump CL3 is also set in the state in which the suction operation is enabled.

Then, the valves SV2, SV3, SV4, and SV6 are opened.

Since a positive pressure is applied beforehand to the sheath fluid container C2, the sheath fluid is discharged from the container C2 to the discharge fluid container C2 through the valve SV6, syringe pump CL1, valve SV4, sheath flow cell FC, and valves SV2 and SV3.

Then, the valves SV2, SV3, SV4, and SV6 are closed.

In this way the sheath fluid is loaded into the syringe pump CL1.

Then, the valves SV3, SV5, and SV7 are opened.

The sheath fluid is discharged from the container C2 to the discharge container C3 through the valve SV7, syringe pump CL3, syringe pump CL2, and valves SV5 and SV3.

Then, the valves SV3, SV5, and SV7 are closed.

In this way the sheath fluid is loaded into the syringe pumps CL2 and CL3.

Then, the valves SV1, SV2, SV4, and SV5 are opened, the stepping motors SM1 and SM2 are driven, and the syringe pump CL1 performs an operation of discharging a flow quantity Q, the syringe pump CL2 performs an operation of suctioning a flow quantity Q, and the syringe pump CL3 performs an operation of suctioning a flow quantity Qs.

In this way a flow quantity Q of sheath fluid flows from the syringe pump CL1 to the sheath flow cell FC, and a flow quantity Qs of sample fluid also flows from the sample container C1 into the sheath flow cell FC. After the sample fluid is converted to a narrow sample fluid flow surrounded in a sheath fluid flow in the sheath flow cell FC, the mixed fluid of the flow quantity (Q+Qs) mixed with the sheath fluid is discharged from the sheath flow cell FC.

Within the discharged mixed fluid, a mixed fluid of flow quantity Q is suctioned by the syringe pump CL2, and a mixed fluid of flow quantity Qs is suctioned by the syringe pump CL3.

At this time, the sample fluid flow formed in the sheath flow cell FC is irradiated by light emitted from the light source LS, and the particles contained in the sample fluid are imaged by the CCD camera VC.

The personal computer 20 shown in FIG. 3 receives the imaging signals from the CCD camera VC and subjects the signals to image processing, recognizes the type and number of particles based on the obtained particle image and performs statistical analysis, and outputs the analysis result to the output unit 25.

Sample Fluid Flow and Stability

The following tests were conducted to confirm the stability of the sample flow quantity relative to changes in the flow quantity of the sheath flow in the particle image analyzer of the present embodiment.

In FIG. 1, with the valves SV1, SV2, SV4, and SV5 in the open state, the syringe pump CL1 was driven by the first drive source 8, and the second syringe pump CL2 was independently drive by the third drive source which is independent from the first drive source 8, and the flow quantity of the syringe pump CL1 was periodically changed by the first drive source 8.

Figure 4:
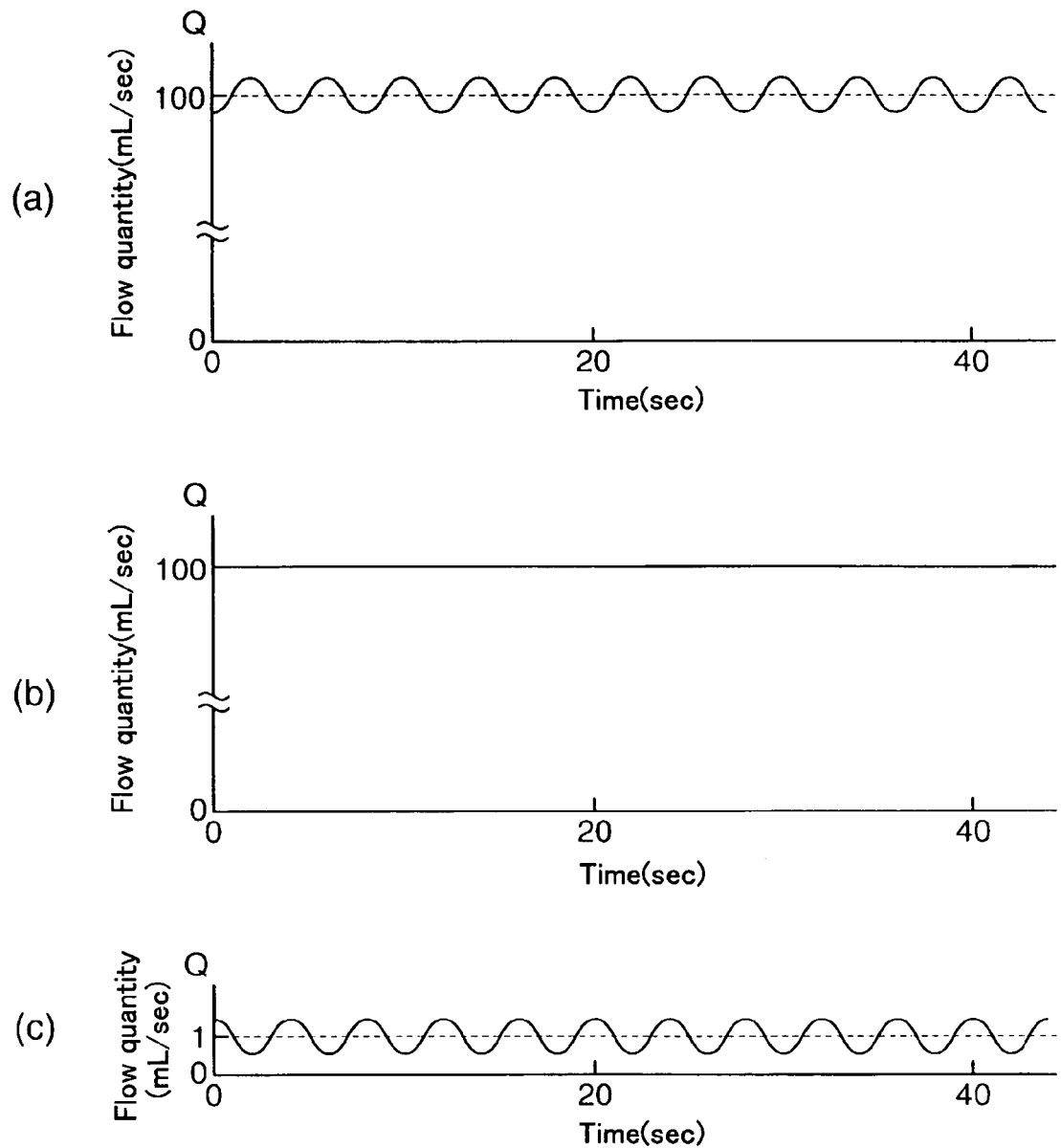
FIG. 4 is a timing chart showing the test result of the embodiment of the sample analyzer.

In FIG. 1, at this time the change over time of the flow quantity Q at point P1 in the flow path between valve SV4 and the discharge port of the syringe pump CL1 is shown in part (a) of FIG. 4.

Furthermore, the change over time of the flow quantity Q at point P2 in the flow path between valve SV5 and the suction port 5a of the syringe pump CL2 is shown in part (b) of FIG. 4. Finally, the change over time of the flow quantity Q at point P3 in the flow path between valve SV1 and the sample fluid inlet 2 is shown in part (c) of FIG. 4.

As shown in part (a) of FIG. 4, the flow quantity Q at point P1 changed about a center of 100 mL/sec with an amplitude of 1 mL/sec and a period of 4 sec.

The flow quantity at point P2 held constant at 100 mL/sec, as shown in part (b) of FIG. 4.

The flow quantity Q at point P3 changed about a center of 100 mL/sec with an amplitude of 1 mL/sec and a period of 4 sec, as shown in part (c) of FIG. 4.

That is, when the flow quantity of either of the syringe pumps CL1 or CL2 changes, the flow quantity Q of the sample fluid is changed only by the amount of the change in the flow quantity. Thus, it can be understood that when the flow quantity of the sheath fluid changes by 0.5%, the flow quantity of the sample fluid changes by ±50%.

In contrast, the syringe pumps CL1 and CL2 were driven by the same drive source 8, and the flow quantities of the syringe pumps CL1 and CL2 changed simultaneously via the drive source 8, as in the specification of the present invention. In this case, the results corresponding to parts (a), (b), and (c) of FIG. 4 are shown in parts (a), (b), and (c) of FIG. 5.

Figure 5:
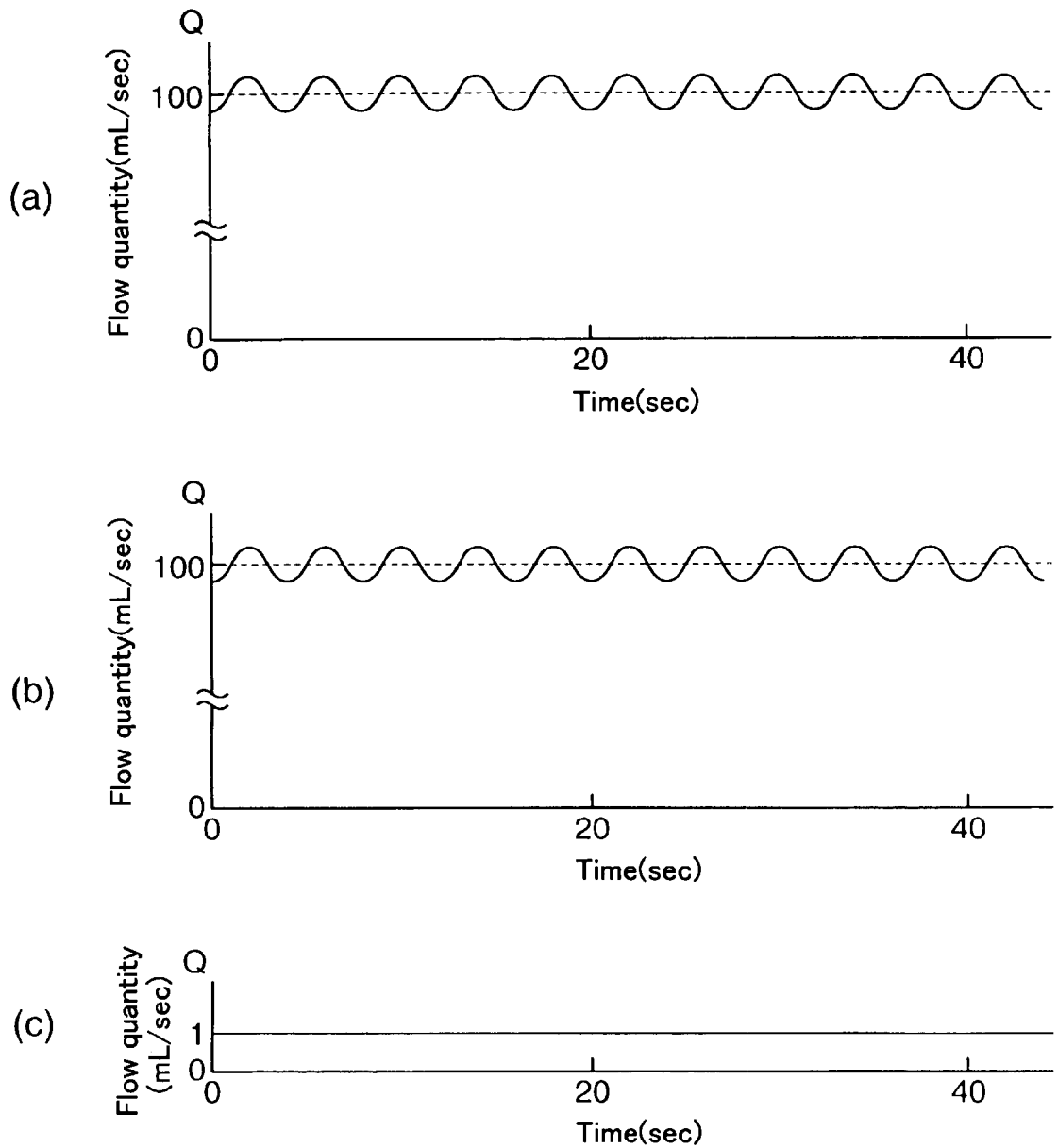
FIG. 5 is a timing chart showing the test results of the embodiment of the sample analyzer.

The flow quantity Q at points P1 and P2 changed about a center of 100 mL/sec with an amplitude of 1 mL/sec and a period of 4 sec, as shown in parts (a) and (b) of FIG. 5.

In this case, the flow quantity Q at point P3 held constant at 100 mL/sec, as shown in part (c) of FIG. 5.

That is, since the syringe pumps CL1 and CL2 are driven by a single drive source 8 in the present invention, even if the flow quantities of the syringe pumps CL1 and CL2 change via a change by the drive source, the change is mutually equal for both, such that the flow quantity of the sample fluid flow remains constant.

Furthermore, since the open topped sample fluid container can be connected to the sample fluid inlet of the sheath flow cell, a mixing device can be inserted so as to easily perform the mixing and dispersion operation of the sample even when the specific gravity of the particles is large and the particles readily precipitate in the sample fluid.

In the above embodiment, analysate particles include tangible components such as are contained in body fluids of humans and lactating animals, organic powders such as food additives, and inorganic powders such as toner and pigments.

Although the rotational movement of the stepping motors is converted to linear movement by a timing belt in the above embodiment, the rotational movement of the stepping motor also may be converted to linear movement by a ball screw or wire.

Although the light source in the above embodiment is a strobe lamp, a white light source, laser light source or the like also may be used. Furthermore, although the strobe lamp is controlled by a driver circuit so as to emit light at a predetermined period, the strobe lamp also may be controlled for continuous light emission via the driver circuit.

A CCD camera is used in the above embodiment imaging particles to detect particles in the sample fluid, however, a camera such as a video camera, or light sensor such as a photodiode, phototransistor, photomultiplier tube and the like also may be used.

The present invention has been described using an example when applied to a particle image analyzer in the above embodiment, however, the present invention is not limited to this example, inasmuch as the present invention also may be applied to flow cytometers which optically or electrically measure various types of particles having diameters from the submicron level to several hundred micron level.

Figure 6:
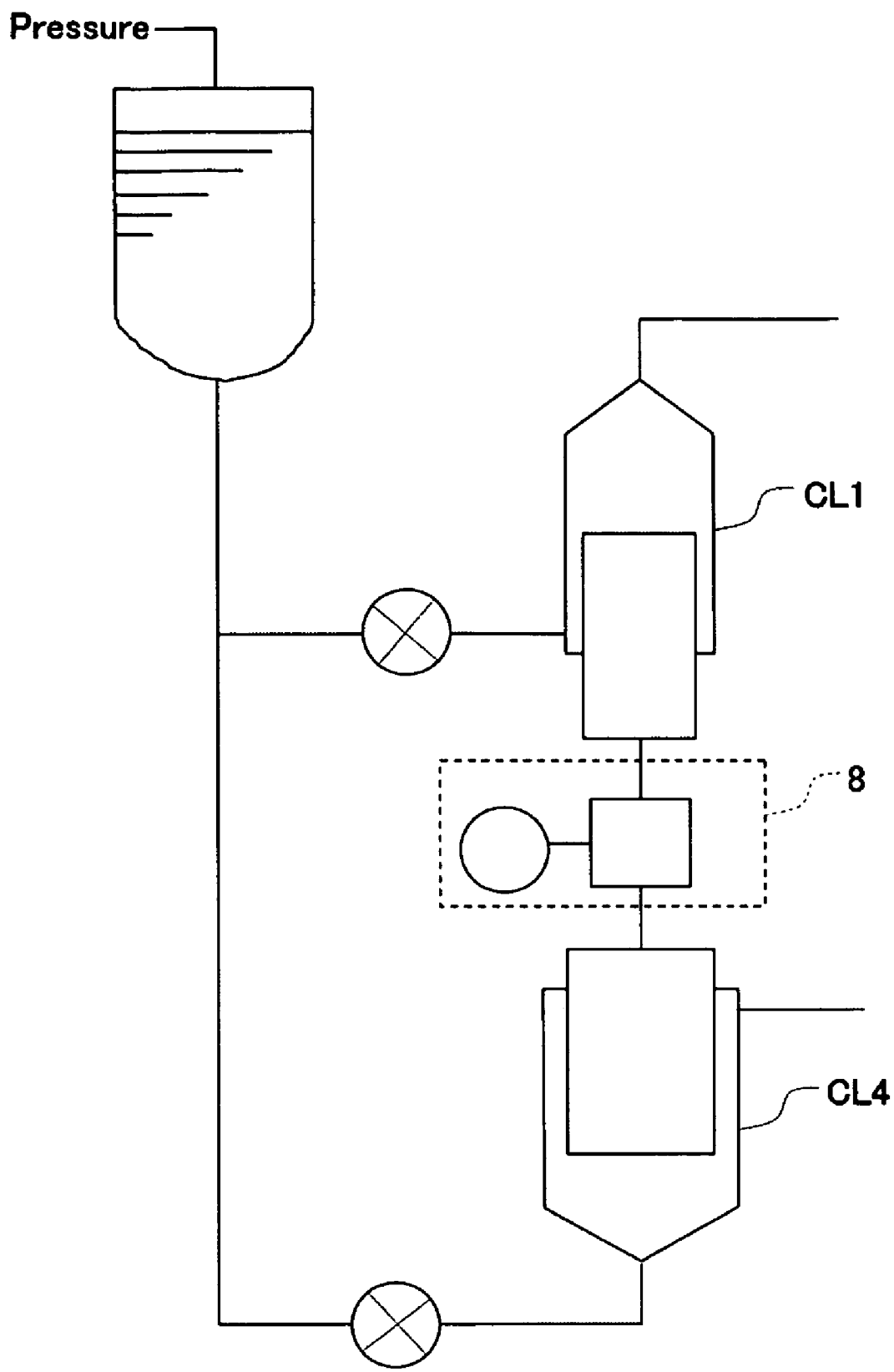
FIG. 6 shows the flow system of a modification of the embodiment of the sample analyzer.

A modification of the above embodiment is described below in an example using a syringe pump CL4 which has a diameter larger than the syringe pump CL1, and which replaces the syringe pump CL2 and syringe pump CL3, as shown in FIG. 6. In FIG. 6, the piston of the syringe pump CL4 has a diameter which is larger than the diameter of the piston of the syringe pump CL1, and the syringe pumps CL1 and CL4 are driven in linkage by a single drive source 8. In other aspects the construction is identical to that of FIG. 1. In this modification, the stepping motor SM1 is driven, and the syringe pump CL1 performs an operation to discharge a flow quantity Q and the syringe pump CL4 performs an operation to suction a flow quantity (Q+Qs), such that the difference in the flow quantities of the syringe pump CL1 and the syringe pump CL4 is the constant suction quantity Qs.

What is claimed is:

1. A sheath flow forming device, comprising:
   a first container that stores sample fluid and has a supply port that supplies the sample fluid;

a second container that stores sheath fluid and has a supply port that supplies the sheath fluid;

a sheath flow cell with a sample fluid inlet that receives sample fluid supplied from the supply port of the first container and forms a flow of the received sample fluid, a sheath fluid inlet that receives the sheath fluid from the supply port of the second container and forms the sheath flow by forming a flow of the received sheath fluid around the sample fluid flow, where a body of the sheath flow cell is concentrically disposed around the sample fluid inlet, and an outlet that discharges the mixture of the sheath fluid and the sample fluid, such that the formed sheath flow flows in the sheath flow cell to the outlet;

a first syringe pump that supplies a sheath fluid to the sheath fluid inlet and has a first piston and a first cylinder;

a second syringe pump that suctions fluid within the flow cell through the outlet of the flow cell and has a second piston linked by a linkage to the first piston and a second cylinder such that the first and second pistons have the same axis and the first piston and the second piston have mutually equal diameters;

a third pump that suctions fluid within the flow cell through the outlet of the flow cell;

a first drive source that simultaneously drives the first pump and second pump by driving the coupled first piston and second piston, such that a first flow quantity of the sheath fluid supplied to the sheath fluid inlet by first pump and a second flow quantity of the mixture discharged from the outlet by the second pump are equal; and a second drive source that drives the third pump.

2. The sheath flow forming device of claim 1, wherein a difference between a first flow quantity of the sheath fluid supplied to the sheath fluid inlet by first pump and a second flow quantity of the mixture discharged from the outlet by the second pump is constant.

3. The sheath flow forming device of claim 1, wherein the top part of the container for storing sample fluid is open to the air.

4. The sheath forming device of claim 1, wherein the first drive source comprises a stepping motor, and a mechanism for converting the rotation of the stepping motor to linear movement.

5. The sheath flow forming device of claim 4, wherein the conversion mechanism comprises one selected from a timing belt, ball screw and wire.

6. The sheath flow forming device of claim 4, wherein the conversion mechanism comprises a timing belt, drive pulley and driven pulley.

7. The sheath flow forming device of claim 1, wherein the third pump is a syringe pump, and the second drive source comprises a stepping motor.

8. The sheath flow forming device of claim 7, wherein the second drive source comprises a mechanism for converting the rotation of the stepping motor to linear movement.

9. The sheath flow forming device of claim 8, wherein the conversion mechanism comprises one selected from a timing belt, and ball screw and wire.

10. The sheath flow forming device of claim 8, wherein the conversion mechanism comprises a timing belt, drive pulley and driven pulley.

11. A sample analyzer, comprising:

a first container that stores sample fluid and has a supply port that supplies the sample fluid;

a second container that stores sheath fluid and has a supply port that supplies the sheath fluid;

a sheath flow cell with a sample fluid inlet that receives sample fluid supplied from the supply port of the first container and forms a flow of the received sample fluid, a sheath fluid inlet that receives the sheath fluid from the supply port of the second container and forms the sheath flow by forming a flow of the received sheath fluid around the sample fluid flow, where the body of the sheath flow cell is concentrically disposed around the sample fluid inlet, and an outlet that discharges the mixture of the sheath fluid and the sample fluid, such that the formed sheath flow flows in the sheath flow cell to the outlet;

a first syringe pump that supplies a sheath fluid to the sheath fluid inlet and has a first piston and a first cylinder;

a second syringe pump that suctions fluid within the flow cell through the outlet of the flow cell and has a second piston linked by a linkage to the first piston and a second cylinder such that the first and second pistons have the same axis and the first piston and the second piston have mutually equal diameters;

a third pump that suctions fluid within the flow cell through the outlet of the flow cell;

a first drive source that simultaneously drives the first pump and second pump by driving the coupled first piston and second piston such that a first flow quantity of the sheath fluid supplied to the sheath fluid inlet by first pump and a second flow quantity of the mixture discharged from the outlet by the second pump are equal;

a second drive source that drives the third pump;

a light source that irradiates with light the sample fluid in the flow cell;

detection unit that detects optical information from the sample fluid; and analysis unit that analyzes the detected optical information.

12. The sample analyzer of claim 11, wherein a difference between a first flow quantity of the sheath fluid supplied to the sheath fluid inlet by first pump and a second flow quantity of the mixture discharged from the outlet by the second pump is constant.

13. The sample analyzer of claim 11, wherein the third pump is a syringe pump, and the second drive source comprises a stepping motor.

* * * * *